United States Patent [19]

Weimel

[11] Patent Number: 5,408,484
[45] Date of Patent: Apr. 18, 1995

[54] SWITCHABLE ENERGY SUPPLY FOR A LASER SYSTEM

[76] Inventor: Erich Weimel, Hahnenweg 5, 8563 Schnaittach, Germany

[21] Appl. No.: 983,164
[22] Filed: Nov. 30, 1992

[30] Foreign Application Priority Data

May 21, 1991 [DE] Germany ........... PCT/DE91/00418

[51] Int. Cl.⁶ .................................................. H01S 3/00
[52] U.S. Cl. .......................................... 372/38; 372/29;
372/81; 372/9; 372/109; 606/4
[58] Field of Search ................... 372/25, 29, 30, 33,
372/38, 108, 81, 82, 85, 109, 9; 606/4, 10, 11

[56] References Cited

U.S. PATENT DOCUMENTS

| | | | |
|---|---|---|---|
| 3,453,490 | 2/1968 | Hallock et al. | 315/170 |
| 3,541,420 | 11/1970 | Rees | 372/82 |
| 4,430,739 | 2/1984 | McMahan | 372/38 |
| 4,590,598 | 5/1986 | O'Harra, II | 372/38 |
| 4,601,037 | 7/1986 | McDonald | 372/38 X |
| 4,648,093 | 3/1987 | Sasnett et al. | 372/38 |
| 4,785,456 | 11/1988 | Kaplan | 372/38 |
| 4,811,188 | 3/1989 | Bees | 372/82 |
| 5,054,029 | 10/1991 | Sugawara et al. | 372/38 |
| 5,119,390 | 6/1992 | Ohmori | 372/38 |
| 5,315,607 | 5/1994 | Nielsen | 385/38 |

FOREIGN PATENT DOCUMENTS

| | | | |
|---|---|---|---|
| 0024268 | 2/1981 | European Pat. Off. | 372/38 X |
| 0230095 | 7/1987 | European Pat. Off. | 372/38 X |

Primary Examiner—Brian Healy
Attorney, Agent, or Firm—Evenson, McKeown, Edwards & Lenahan

[57] ABSTRACT

A laser system has a laser which can be switched between at least two power settings and an energy supply unit for the laser, with the supply input voltage applied at said energy supply unit being mains voltage. The present invention is distinguished by the energy supply unit having a distribution unit at whose input connection main voltage is applied and which is connected to a laser power unit and a charge unit for an accumulator unit in such a manner that during the time that the laser is operated with low power the charge unit is also supplied with energy from the electric mains in addition to the laser power unit and that during the time that the laser is operated with high power the output connection of the accumulator unit is connected to the laser power unit.

11 Claims, 2 Drawing Sheets

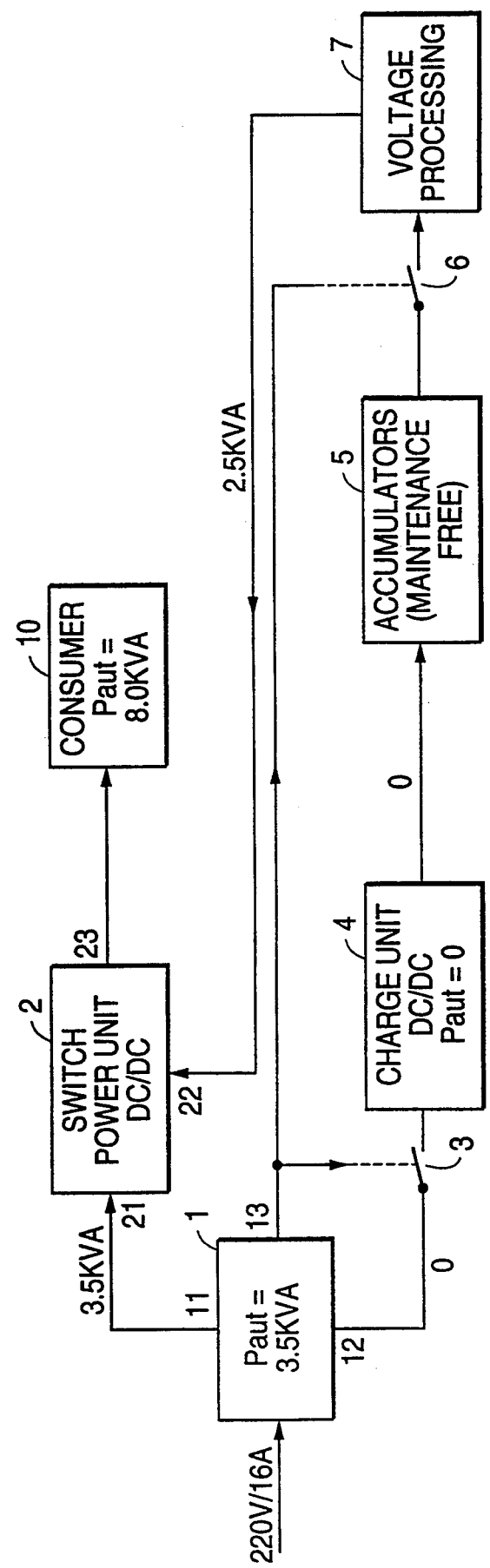

SWITCHABLE ENERGY SUPPLY FOR A LASER SYSTEM

This application is a continuation of PCT application Ser. No. PCT/DE91/00418, filed May 21, 1991, and now abandoned.

BACKGROUND AND SUMMARY OF THE INVENTION

The present invention relates to a laser system having a laser, which can be switched between at least two power settings, and an energy supply unit for the laser, with the supply input voltage applied at the energy supply unit being mains voltage.

Laser systems of this type are commonly known for example argon or krypton lasers having at least two power settings are utilized in ophthalmology for fundus oculi coagulation.

In both known lasers, the low power setting is designed in such a manner that the laser beam is preceived on the fundus oculi but does not cause coagulation; in this way the laser can be focused onto the area to be treated. By switching the laser to the high power setting, the desired treatment of the fundus oculi is obtained.

However, some lasers, such as, argon lasers display relatively poor effectivity. Thus the energy supply unit for this laser must be designed in such a manner that it has relatively high maximum power,—usually 5 kW to 10 kW—in order to be able to operate the laser with therapeutically effective power. Energy supply units with such maximum power can, however, no longer be connected to the "normal" electric mains as electric outlets for 220 V are usually fused with only 16 A so that power no greater than 3.5 kW can be drawn. Moreover, many of the conventional commercial energy supply units for argon lasers with therapeutically effective power are water-cooled.

This usually means that argon treatment lasers cannot be installed in physicians' offices without special installation measures—three-phase current outlets, water supply lines, etc.

An object of the present invention is to improve a laser system which can be switched between two particular settings and, in particular, an argon treatment laser, by way of illustration, for ophthalmological applications in such a manner that the energy supply unit of the laser system has maximum power take up which allows supply from typical house installation electric mains.

The present invention is based on the understanding that generic laser systems usually are only operated for a relatively short period of time with high power. By way of illustration, in the case of argon laser systems for fundus oculi treatment, the duration of the therapeutically effective "laser shots" lies in the seconds range and below, with several minutes often passing between the individual "laser shots", during which the physician checks the alignment of the fundus oculi and/or the success of the treatment.

For this reason, in accordance with the present invention the energy supply unit is designed in such a manner that it does not, by way of illustration, draw the maximum power required for therapeutically effective "laser pulses" solely from the electric mains, but—partially—from an energy storage means which is recharged during the time that the laser is not in operation, respectively is operating with low power.

For this purpose the energy supply unit has a distribution unit at the input connection of which the mains voltage is applied and which is connected with a laser power unit and a charge unit for an accumulator unit in such a manner that during the time that the laser is being operated with low power that both the laser power unit and the charge unit are supplied with energy from the electric mains and that during the time that the laser is being operated with high power the output connection of the accumulator unit is connected to the laser power unit.

According further to the present invention, the distribution unit interrupts the connection electric mains/accumulator unit during the time that the laser is being operated with high power, the entire power that can be drawn from the electric mains is utilized for supplying the laser so that the accumulator unit only has to provide the difference between the "peak power" required for the therapeutically effective laser pulse and the maximum power that can be drawn from the electric mains.

According further to the present invention, the laser power unit is a DC/DC switching power unit and the charge unit is a DC charge unit. By this means it is possible "to work" with direct current in the energy supply unit after the distribution unit so that no transformation to alternating current is required of the accumulator output voltage.

Possible necessary "adaptions" can be easily carried out by connecting a voltage transformer between the output connection of the acculator unit and the input connection of the laser power unit.

The invented concept for providing the additional power required for high power in switchable lasers can be utilized in any laser system.

A particular advantage of the invented concept is, however, with argon laser systems utilized for therapeutical purposes, as by way of illustration for fundus oculi coagulation. Lasers designed according to the present invention can be connected to normal conventionally fused electric outlets without any special "installation measures" and in particular do not require water cooling for the energy supply unit.

It is not necessary that the low power setting in which the laser is continually supplied with energy from the electric mains is a power setting in which the laser emits a laser beam. But rather the invented design is advantageous especially in a laser system in which the low power setting is a stand-by modus in which the laser tube is operated below the laser threshold. A system of this type is described in an application of the same applicant filed on the same day: in this system the beam of the argon laser is not used for alignment. But rather the beam of a target beam laser, by way of illustration a helium neon laser, which has good effectivity and thus low power take up is directed co-axially to the path of the argon laser beam. The helium-neon laser beam is employed to align the argon laser. The argon laser is operated in the so-called stand-by mode below the laser threshold so that a therapeutically effective laser beam can be triggered without any delay. In the stand-by modus the power take up of the laser tube is particularly low so that the accumulator can be charged in a short time.

Other objects, advantages and novel features of the present invention will become apparent from the following detailed description of the invention when considered in conjunction with the accompanying drawings.

DESCRIPTION OF A PREFERRED EMBODIMENT

Figure 1:
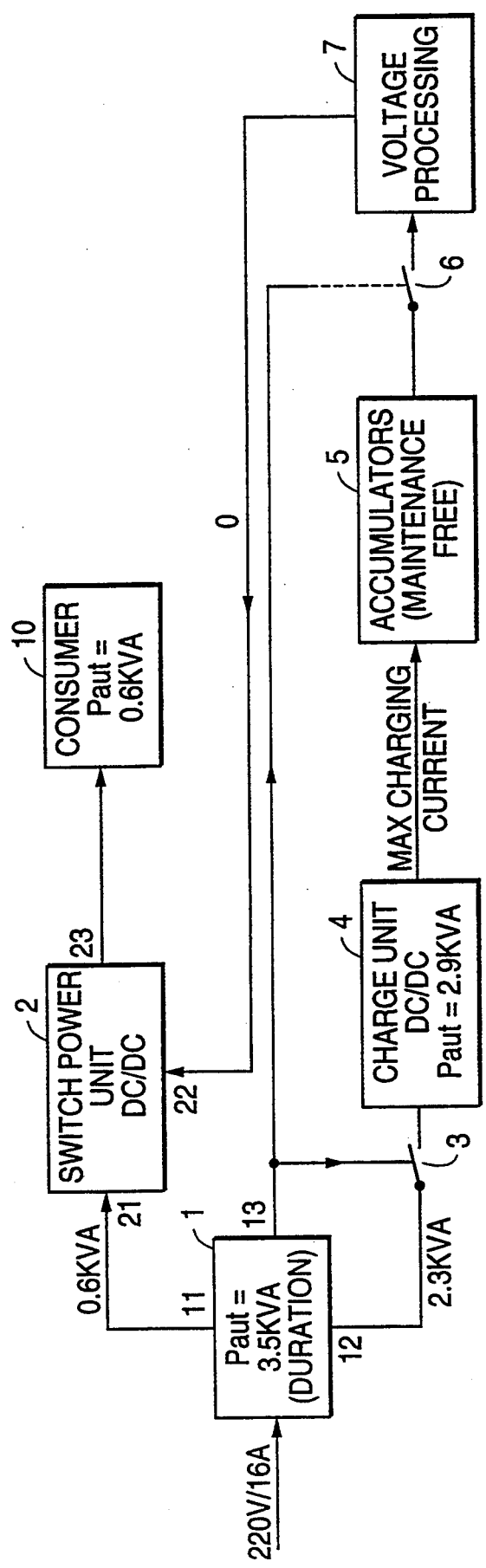

An energy supply unit of an invented laser system is schematically depicted in the Figures. The actual laser having a laser tube, laser mirrors and a pump unit, which usually is a continous-line argon laser for ophthalmological treatment, is only schematically referred to as consumer 10.

The energy supply unit is designed in such a manner that it can be operated with a 220 V electric outlet conventionally fused with a 16 fuse. The alternating voltage is applied to a distribution unit 1 which has two load output connections 11 and 12 and a control output connection 13. Preferably an AC/DC tranformation takes place in the distribution unit so that a voltage which can be "further processed" in the DC/DC switch power unit is applied at the output connections 11 and 12.

The output connecton 11 of the distribution unit 1 is connected to an input connection 21 of a DC/DC switch power unit 2 whose output connection 23 is connected to the previously mentioned actual laser 10. The other output connection 12 is connected to the input connection of a charge unit 4 for the accumulator unit 5 via a switch 3. The output connection of accumulator unit 5 is connected via another switch 6 to a voltage processing cicuit 7 which for its part is connected to another input connection 22 of the switch power unit 2. The accumulator unit is a unit built from a conventional commercial and, in particular, maintenance-free lead, NiCd accumulators or the like, in which the individual accumulators are connected in series or in parallel. The voltage processing circuit 7 essentially fulfills the function of processing the output direct voltage of the accumulator unit 5 in such a manner that a circuit suited as input voltage is yielded for the switch power unit 2.

The distribution unit 1 furthermore controls the switches 3 and 6 via the control connection 13.

The function of the described energy supply unit is described in the following section:

FIG. 1 shows the current flow in the so-called standby operation, in which the laser tube of the argon laser 10 is operated below the laser threshold. Although the laser does not emit a laser beam in this type of operation, it is instantly ready for operation if, by way of illustration, a physician wants to trigger a therapeutically effective laser pulse by pressing a foot switch (not shown). In this type of operation, the distribution unit 1 distributes the power of 220 V * 16 A 3.5 kW drawn from the electric mains in such a manner that 0.6 kW are delivered to the switch power unit 2 and 2.9 kW via the closed switch 3 to charge unit 4. As in this type of operation the switch 6 is open, charge unit 4 charges the accumulator unit 5 until it is fully charged.

Although the power delivered to switch power unit 2 does not suffice to reach the laser threshold of the laser tube, it is enough to maintain the laser tube in a state from which it can emit a therapeutetically effective laser pulse without any significant delay.

If such a laser pulse is to be emitted, the distribution unit 2 opens the switch 3; in this way the entire power of 3.5 kW drawn from the electric mains is applied at the switch power unit 2. Furthermore, the distribution unit 1 closes the switch 6 so that the output voltage of the accumulator unit 5, suitably processed, is applied at the switch unit 2. In the depicted preferrred embodiment, a power of 2.5 kW can be drawn from the accumulator unit 5 for at least the usual duration of a laser pulse required for ophthalmic purposes, which has at the most a range of a few seconds, so that the laser tube can be operated with a total power of 6 kW.

The present invention has been described in the previous section using a preferred embodiment without the intention of limiting the scope or spirit of the overall inventive idea. By way of illustration, other laser tubes besides argon laser tubes can be employed. Other components can also be utilized such as, by way of illustration, other power units instead of switch power units. Furthermore, the given magnitudes are to be understood to be by way of example. Thus of course the power distribution has to be different, by way of illustration, for 110 V electric mains or differently fused electric mains.

Although the invention has been described and illustrated in detail, it is to be clearly understood that the same is by way of illustration and example, and is not to be taken by way of limitation. The spirit and scope of the present invention are to be limited only by the terms of the appended claims.

What is claimed is:

1. An energy supply unit, for a laser which can be switched between at least two power settings, comprising:
   an energy distribution unit, for receiving electrical energy from a voltage mains;
   a laser power unit, for receiving a first energy supplied from the energy distribution unit and for providing the first energy to the laser;
   a charge unit for receiving energy from the energy distribution unit;
   a rechargeable battery, for receiving energy from the charge unit and for providing a second supplemental energy to the power unit during the time that the laser is operated at the higher of the at least two power settings; and
   a switch, controlled by the distribution unit, for interrupting the connection of the distribution unit to the charge unit during the time that the laser is operated at the higher of the at least two power settings.

2. An energy supply unit, according to claim 1, wherein said laser power unit is a D/C switching power supply and the charge unit is a D/C charge unit.

3. An energy supply unit, according to claim 2, further comprising a voltage processing unit connected between the accumulator unit and the laser power unit.

4. An energy supply unit, according to claim 3, wherein the laser is an argon laser used for ophthalmic purposes.

5. An energy supply unit, according to claim 4, wherein the lower of the at least two power settings is a standby mode in which the tube of the laser is operated below the laser threshold.

6. An energy supply unit, for a laser which can be switched between at least two power settings, comprising:
   an energy distribution unit, for receiving electrical energy from a voltage mains;
   a laser power unit, for receiving energy from the energy distribution unit and for providing energy to the laser;
   a charge unit for receiving energy from the energy distribution unit; and a charge accumulator unit, for receiving energy from the charge unit and for providing energy to the power unit during the time that the laser is operated at the higher of the at least two power settings;

a switch, controlled by the distribution unit, for interrupting the connection of the distribution unit to the charge unit during the time that the laser is operated at the higher of the at least two power settings; and wherein said laser power unit is a D/C switching power supply and the charge unit is a D/C charge unit.

7. An energy supply unit, according to claim 6, further comprising a voltage processing unit connected between the accumulator unit and the laser power unit.

8. An energy supply unit, according to claim 7, wherein the laser is an argon laser used for ophthalmic purposes.

9. An energy supply unit, according to claim 8, wherein the lower of the at least two power settings is a standby mode in which the tube of the laser is operated below the laser threshold.

10. An energy supply unit, according to claim 1, wherein the laser is an argon laser used for ophthalmic purposes.

11. An energy supply unit, according to claim 10, wherein the lower of the at least two power settings is a standby mode in which the tube of the laser is operated below the laser threshold.

* * * * *